United States Patent [19]
Ross et al.

[11] Patent Number: 5,892,097
[45] Date of Patent: Apr. 6, 1999

[54] PROCESS FOR THE PREPARATION OF SUBSTITUTED HYDROXYHYDROCINNAMATE ESTERS

[75] Inventors: John R. Ross, Mobile, Ala.; Michael E. Schultz, Houston, Tex.; Benoît Dubuis, Muttenz; Peter Küng, Gipf-Oberfrick, both of Switzerland

[73] Assignee: Ciba Specialty Chemicals Corporation, Tarrytown, N.Y.

[21] Appl. No.: 862,034

[22] Filed: May 22, 1997

Related U.S. Application Data

[60] Provisional application No. 60/018,184, May 23, 1996.
[51] Int. Cl.⁶ .................................................... C07C 69/76
[52] U.S. Cl. ............................................................ 560/75
[58] Field of Search ................................................ 560/75

[56] References Cited

U.S. PATENT DOCUMENTS 4,594,444 6/1986 Orban .

FOREIGN PATENT DOCUMENTS

| 0300055 | 1/1989 | European Pat. Off. . |
| 0358157 | 3/1990 | European Pat. Off. . |
| 421928 | 4/1991 | European Pat. Off. . |
| 0448775 | 10/1991 | European Pat. Off. . |

*Primary Examiner*—Paul J. Killos
*Attorney, Agent, or Firm*—Luther A. R. Hall

[57] ABSTRACT

The transesterification of substituted lower alkyl hydroxyhydrocinnamates with a higher alcohol or a polyol is greatly facilitated by the use of a trace amount of a tin catalyst. In many cases, the amount of the catalyst is so small that it is unnecessary to remove it from the final product by distillation of said product.

20 Claims, No Drawings

PROCESS FOR THE PREPARATION OF SUBSTITUTED HYDROXYHYDROCINNAMATE ESTERS

This application claims the benefit under 35 USC 119(e) of U.S. Provisional Application No. 60/018,184, filed May 23, 1996.

This invention pertains to an improved process for making substituted higher aliphatic esters of hydroxyhydrocinnamates by transesterification of the corresponding lower alkyl ester using a very small amount of a tin catalyst.

BACKGROUND OF THE INVENTION

The aliphatic esters and polyesters of substituted sterically hindered hydroxyhydrocinnamic acid are well-known as effective antioxidants for a wide variety of organic materials protecting them from oxidative and thermal degradation. Many of these esters have gained wide commercial acceptance as phenolic antioxidants.

Some transesterification catalysts which may be used to prepare the instant compounds include lithium amide, aluminum isopropylate and dibutyltin oxide. U.S. Pat. No. 4,594,444 (Orban) teaches a process for the preparation of sterically hindered hydroxyphenylcarboxylic acid esters by the transesterification of the corresponding methyl or ethyl ester with a higher aliphatic alcohol using an oxide or an organometallic compound of a metal of the fourth main group or subgroup of the periodic table as catalyst in an amount between 0.05 and 1.0 mol percent based on the methyl or ethyl ester. Higher dialkyltin oxides, particularly dibutyltin oxides, are taught as the preferred catalyst for this process.

However, if the amount of tin residue in the product is too high, ultimate product stability is compromised and efforts must be taken to remove such residues. If the amount of tin catalyst can be reduced well below that seen in the Orban process, such residue removal efforts may be unnecessary and process economies would be evident. That is the case in the instant process where the amount of tin catalyst required is so small that its removal from the final product by distillation of said product is often unnecessary.

The instant process differs from this Orban process by running the transesterification process at much lower concentrations of tin catalyst and also at lower temperature.

DETAILED DISCLOSURE

The instant invention pertains to an improved process for the preparation of esters of substituted hydroxyhydrocinnamic acid by the tranesterification of the corresponding methyl or ethyl ester with a higher aliphatic alcohol using small amounts of a tin catalyst.

More particularly, the instant invention involves an improved process for the preparation of a compound of formula I

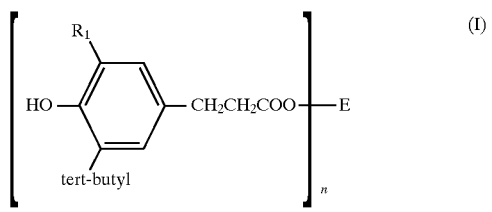

wherein
$R_1$ is alkyl of 1 to 4 carbon atoms,
n is 1 to 4,
when n is 1, E is a straight or branched chain alkyl of 4 to 18 carbon atoms;
when n is 2, E is a straight or branched chain alkylene of 2 to 12 carbon atoms, or said alkylene interrupted by one to five O or S atoms;
when n is 3, E is a straight or branched chain alkanetriyl of 3 to 6 carbon atoms; and
when n is 4, E is pentaerthyrityl;
by reaction of the corresponding lower alkyl ester with an alkanol or polyol of the formula E-(OH)$_n$ wherein the improvement comprises
carrying out the transesterification in the presence of 10 to 250 ppm of a tin catalyst, based on the starting lower alkyl ester, at a temperature of 110°–230° C.

Preferably, the lower alkyl ester is a compound of formula I where n is 1 and E is methyl or ethyl; most preferably methyl.

Preferably, $R_1$ is methyl or tert-butyl.

When n is 1, E is preferably alkyl of 8 to 18 carbon atoms; most preferably isooctyl, lauryl or n-octadecyl; especially n-octadecyl.

When n is 2, E is preferably hexamethylene, —CH$_2$CH$_2$SCH$_2$CH$_2$— or —CH$_2$CH$_2$OCH$_2$CH$_2$OCH$_2$CH$_2$—.

When n is 3, E is preferably CH$_3$C(CH$_2$—)$_3$ or CH$_3$CH$_2$C(CH$_2$—)$_3$.

Preferably, the temperature is 150°–190° C., most preferably 160°–190° C.

Preferably, the tin catalyst is a monoalkyltin ester, a dialkyltin ester, a dialkyltin oxide, a trialkyltin oxide, tin tetrachloride, a monoalkyltin trichloride, a dialkyltin dichloride, a trialkyltin chloride, a diaryltin dichloride or a stannous tin ester.

Most preferably, the tin catalyst is butyltin tris(2-ethylhexanoate); dibutyltin bis(2-ethylhexanoate); dibutyltin diacetate; dibutyltin oxide, trioctyltin oxide; butyltin trichloride; butyltin trimethylate; dibutyltin dichloride; diphenyltin dichloride; tributyltin chloride or stannous bis (2-ethylhexanoate); especially butyltin tris-(2-ethylhexanoate), dibutyltin diacetate, butyltin trichloride, butyltin trimethylate or dibutyltin oxide.

It is noted that tin compounds other than those specifically listed above may also be effective catalysts for the instant transesterification reaction.

The instant process is conveniently run at a pressure of between 250 and 1 mbar; preferably between 50 and 3 mbar.

Although the instant process is preferably run without the presence of an inert solvent or stripping agent, the process works equally well when such an inert solvent or an inert gas stripping agent such as nitrogen is used.

The instant transesterification process is an improved process over that of Orban since it can be catalyzed by the use of a tin catalyst, especially butyltin tris-2-ethylhexanoate at levels between 10–250 ppm Sn catalyst based on the starting methyl or ethyl ester. The reaction goes to at least 98% completion with these tiny amounts of catalyst. The low catalyst level and high conversion rate eliminate the necessity for post-reaction separation of either catalyst or unreacted starting materials from the final ester product. Elimination of any post-reaction work-up significantly reduces production costs by reducing cycle time and elimination costs associated with waste disposal. Clear economies attend the instant process.

Preferably, the amount of tin catalyst is 25–100 ppm Sn. In the case where in formula I, n is 4 and E is pentaerythrityl, the amount of tin catalyst is preferably 200–250 ppm Sn.

As mentioned above, relatively high levels of transesterification catalysts are used in the industry necessitating removal of catalyst residues from the final product. Failure to remove such catalyst residues may have deleterious effects on both the stability of the instant product itself and on its performance in end-use applications as a phenolic antioxidant. Prior art transesterification catalysts such as lithium amide, lithium methoxide and aluminum isopropylate must be used at levels ranging from 200–500 ppm of lithium or aluminum, based on the starting methyl or ethyl ester, in order to achieve acceptable conversions to final product (at least 97%).

By contrast the instant invention uses dibutyltin oxide or butyltin tris-2-ethyl-hexanoate at a level of 10–250 ppm Sn. In most cases, except for the compound where n is 4 and E is pentaerythrityl which requires 200–250 ppm Sn catalyst, this leaves a level of tin in the final product of 100 ppm or less. Tin at these levels are shown to have no negative effects on either product stability or on final product performance in end-use applications. The instant improved process clearly eliminates any need for a post-reaction catalyst residue removal, typically acid neutralization of the basic catalysts (i.e. lithium amide or lithium methoxide) followed by repeated water washes or the use of an aqueous alkaline solution to precipitate the tin catalysts as their hydroxides. Alternatively, the separation of the hydroxyhydrocinnamate esters from the catalyst residue can be performed by an expensive operation such as distillation or crystallization of the ester. The instant process is a significant improvement over the processes of the prior art.

The following experiments are not to be construed to limit the scope of the instant invention in any manner whatsoever.

EXAMPLE 1

Isooctyl 3,5-Di-tert-butyl-4-hydroxyhydrocinnamate

In a three-necked, round-bottomed flask fitted with a stirrer, thermometer, reflux condenser with a trap to collect distilled off methanol and later isooctanol and a vacuum connection are added 200 g (0.684 mole) of methyl 3,5-di-tert-butyl-4-hydroxyhydrocinnamate, 178 g (1.37 moles, 100% excess) of isooctanol (Exxal®-8, Exxon) and 0.05 g (0.0000826 mole; 50 ppm of tin in final product) of butyltin tris-(2-ethylhexanoate) (Fascat® 9102, Elf-Atochem). The reaction mixture is subjected to a reduced pressure of 400 mm Hg and the flask is heated to 140°–150° C. Methanol begins to be evolved and is collected in the trap receiver. When the reaction mixture reaches 160° C., reflux of isooctanol is observed and becomes vigorous at 170°–180° C. while the evolution of methanol subsides. At this point, the excess isooctanol is then stripped into the trap receiver and the pressure in the system is ultimately reduced to 5 mm Hg. When all the excess isooctanol is removed, the residue in the flask is cooled under nitrogen and is the desired title compound in essentially quantitative yield (over 99% by weight).

The product is "water-white" and contains less than 1% by weight of starting methyl ester and less than 0.1% by weight of isooctanol.

EXAMPLE 2

Isooctyl 3,5-Di-tert-butyl-4-hydroxyhydrocinnamate

Following the general procedure of Example 1, using a 100% excess of isooctanol, a reaction time of 65 minutes and sufficient catalyst to leave 77 ppm of tin in the final product, a conversion of 99.8% to the title compound is obtained with only 0.2% of the starting methyl ester as an impurity (by GC area %). No isooctanol is seen in the final product.

EXAMPLE 3

Isooctyl 3,5-Di-tert-butyl-4-hydroxyhydrocinnamate

Following the general procedure of Example 1, using a 60% excess of isooctanol, a reaction time of 65 minutes and sufficient catalyst to leave 61 ppm of tin in the final product, a conversion of 99.6% to the title compound is obtained with only 0.4% of the starting methyl ester as an impurity (by GC area %). No isooctanol is seen in the final product.

EXAMPLE 4

Isooctyl 3,5-Di-tert-butyl-4-hydroxyhydrocinnamate

Following the general procedure of Example 1, using a 60% excess of isooctanol, a reaction time of 60 minutes and sufficient catalyst to leave 42 ppm of tin in the final product, a conversion of 98.2% to the title compound is obtained with only 1.7% of the starting methyl ester as an impurity (by GC area %). No isooctanol is seen in the final product.

EXAMPLE 5

Isooctyl 3,5-Di-tert-butyl-4-hydroxyhydrocinnamate

Following the general procedure of Example 1, using a 100% excess of isooctanol, a reaction time of 90 minutes and sufficient catalyst to leave 20 ppm of tin in the final product, a conversion of 97.9% to the title compound is obtained with only 2.0% of the starting methyl ester as an impurity (by GC area %). 0.1% of isooctanol is seen in the final product (by GC area %).

Examples 1–5 show that even when the concentration of catalyst is reduced to a level leaving only 20 ppm of tin in the final product, the conversion to final product goes expeditiously to levels of at least 97% and at lower temperatures than needed in the Orban process.

EXAMPLES 6–8

Using the general procedure of Example 1 with either the methyl or ethyl ester of a substituted hydroxyhydrocinnamic acid and various alkanols, the following higher esters of formula I are obtained in high yield and purity.

| Example | $R_1$ | E |
|---|---|---|
| 6 | tert-butyl | lauryl |
| 7 | tert-butyl | n-octadecyl |
| 8 | tert-butyl | n-octyl |

EXAMPLE 9

Isooctyl 3,5-Di-tert-butyl-4-hydroxyhydrocinnamate

When following the general procedure of Example 1, and substituting a like mol % amount of dibutylin oxide for the butyltin tris-(2-ethylhexanoate) as catalyst, the title compound is obtained without the need for further purification of said product by distillation.

EXAMPLE 10 n-Octadecyl 3,5-Di-tert-butyl-4-hydroxyhydrocinnamate

In a reactor fitted with a heating/cooling bath, stirrer, thermocouple, nitrogen inlet, a reflux condenser with a trap to collect distilled off methanol, and a vacuum connection are added 438.6 g (1.5 moles, a 5% excess) of methyl 3,5-di-tert-butyl-4-hydroxyhydrocinnamate and 386.8 g (1.43 moles) of 1-octadecanol. The mixture is heated to 100° C. under nitrogen with stirring. After drying at 100° C. under vacuum ($\leq$5 mm Hg) for 30 minutes, the mixture is heated to 120° C. under nitrogen and 0.05 g (0.0002 mole) of dibutyltin oxide (Fascat® 4201, Elf-Atochem) is added. The vacuum is lowered to 100 mm Hg and the reaction mixture is heated to 185° C. for one hour. The vacuum is slowly lowered to 2 mm Hg over 1.5 hours and kept at that temperature and pressure for another thirty minutes. The vacuum is broken with nitrogen and the reaction mass is cooled to 100° C. The excess methyl 3,5-di-tert-butyl-4-hydroxyhydrocinnamate is removed using a wiped-film evaporator to give the title compound as a white solid containing 30 ppm Sn. Essentially a quantitative yield (99.8) of the ester product is obtained.

This 30 ppm of Sn residue is acceptable in all application tests for this ester antioxidant.

EXAMPLE 11

Pentaerythrityl Tetrakis(3,5-di-tert-butyl-4-hydroxyhydrocinnamate)

Following the general procedure of Example 10, the title compound is prepared using 725 g (2.48 moles) of methyl 3,5-di-tert-butyl-4-hydroxyhydrocinnamate and 67.5 g (0.50 mole) of pentaerythritol and 0.30 g (0.0012 mole) of dibutyltin oxide (Fascat® 4201, Elf-Atochem). The reaction mixture is heated from 120° C. to 190° C. over thirty minutes at 100 mm Hg, then at 190° C. the pressure is lowered to 3 mm Hg over a two hour period. The reaction mixture is heated at 190° C. for another three hours. The excess methyl 3,5-di-tert-butyl-4-hydroxyhydrocinnamate is removed by distillation at 205° C. at $\leq$1 mm Hg to give an excellent yield of the title compound as a white solid containing 200 ppm Sn.

Analysis of the product obtained shows it to be approximately 96.5% of the title compound, 2.0% of the corresponding triester and 0.7% of the starting methyl ester.

In this case, since the level of tin catalyst residue is 200 ppm Sn, removal of the tin catalyst residue can be effected by distillation where the tin catalyst stays in the bottoms; or by recrystallization where the tin catalyst stays in the mother liquors. Both such operation are expensive.

To remove the tin catalyst from the hydroxyhydrocinnamate ester melt, commonly an aqueous alkaline solution is used to form an insoluble tin hydroxide. However, it is known that an alkaline medium is deleterious to such ester products resulting in yellow color formation and degradation of the ester product.

For each of the reasons given above, such methods for the separation of tin catalyst residues are to be avoided whenever the level of tin catalyst residue is not detrimental to the performance of the ester antioxidant in end-use applications. The instant process affords such a method to avoid the need for later tin catalyst removal in most situations.

EXAMPLE 12

2,2'-Thiodiethylene Bis(3,5-di-tert-butyl-4-hydroxyhydrocinnamate)

Using the general procedure of Example 11, 731 g (2.5 moles) of methyl 3,5-di-tert-butyl-4-hydroxyhydrocinnamate, and 150 g (1.23 moles) of 2,2'-thiodiethanol are heated to 120° C. Then, 0.26 g of dibutyltin diacetate (Fascat® 4200, Elf-Atochem, calculated 98 ppm Sn), is added and a vacuum of <50 mm Hg is imposed . The reaction mixture is heated to 160° C. The vacuum is reduced to <5 mm Hg and the reaction mixture is heated at 160° C. for a total of 7 hours. The vacuum is broken and the temperature is reduced to 100° C. to yield the title compound after crystallization from aqueous isopropanol. The product exhibited excellent transmission >99% at 425 nm.

EXAMPLE 13–18

Using the general procedure of Example 10 with either the methyl or ethyl ester of a substituted hydroxyhydrocinnamic acid and various polyols, the following higher esters of formula I are obtained in high yield and purity.

| Example | n | R$_1$ | E |
|---|---|---|---|
| 13 | 2 | tert-butyl | hexamethylene |
| 14 | 2 | methyl | —CH$_2$CH$_2$SCH$_2$CH$_2$— |
| 15 | 2 | tert-butyl | —CH$_2$CH$_2$(OCH$_2$CH$_2$)$_2$— |
| 16 | 3 | tert-butyl | CH$_3$C(CH$_2$—)$_3$ |
| 17 | 3 | tert-butyl | CH$_3$CH$_2$C(CH$_2$—)$_3$ |
| 18 | 4 | methyl | pentaerythrityl |

What is claimed is:

1. An improved process for the preparation of a compound of formula I

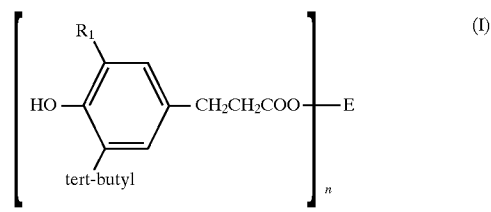

wherein
  R$_1$ is alkyl of 1 to 4 carbon atoms,
  n is 1 to 4,
  when n is 1, E is a straight or branched chain alkyl of 4 to 18 carbon atoms;
  when n is 2, E is a straight or branched chain alkylene of 2 to 12 carbon atoms, or said alkylene interrupted by one to five O or S atoms;
  when n is 3, E is a straight or branched chain alkanetriyl of 3 to 6 carbon atoms; and
  when n is 4, E is pentaerthyrityl;
  by reaction of the corresponding lower alkyl ester with an alkanol or polyol of the formula E—(OH)$_n$ wherein the improvement comprises
  carrying out the transesterification in the presence of 10 to 250 ppm of a tin catalyst, based on the starting lower alkyl ester, at a temperature of 110°–230° C.

2. A process according to claim 1 where the lower alkyl ester is methyl or ethyl 3,5-di-tert-butyl-4-hydroxyhydrocinnamate.

3. A process according to claim 2 where the lower alkyl ester is methyl 3,5-di-tert-butyl-4-hydroxyhydrocinnamate.

4. A process according to claim 1 where in the compound of formula I, R$_1$ is methyl or tert-butyl.

5. A process according to claim 1 where in the compound of formula I, n is 1, and E is alkyl of 8 to 18 carbon atoms.

6. A process according to claim 5 wherein E is isooctyl, lauryl or n-octadecyl.

7. A process according to claim 6 wherein E is n-octadecyl.

8. A process according to claim 1 where in the compound of formula I, n is 2 and E is hexamethylene, —CH$_2$CH$_2$SCH$_2$CH$_2$— or —CH$_2$CH$_2$OCH$_2$CH$_2$OCH$_2$CH$_2$—.

9. A process according to claim 1 where in the compound of formula I, n is 3 and E is CH$_3$C(CH$_2$—)$_3$ or CH$_3$CH$_2$C(CH$_2$—)$_3$.

10. A process according to claim 1 wherein the compound of formula I is
isooctyl 3,5-di-tert-butyl-4-hydroxyhydrocinnamate,
n-octadecyl 3,5-di-tert-butyl-4-hydroxyhydrocinnamate, or
pentaerythrityl tetrakis(3,5-di-tert-butyl-4-hydroxyhydrocinnamate).

11. A process according to claim 1 wherein the amount of catalyst is 25–100 ppm Sn.

12. A process according to claim 1 wherein the amount of catalyst is 200–250 ppm Sn.

13. A process according to claim 1 wherein the tin catalyst is a monoalkyltin ester, a dialkyltin ester, a dialkyltin oxide, a trialkyltin oxide, tin tetrachloride, a monoalkyltin trichloride, a dialkyltin dichloride, a trialkyltin chloride, a diaryltin dichloride or a stannous tin ester.

14. A process according to claim 13 wherein the tin catalyst is butyltin tris(2-ethylhexanoate); dibutyltin bis(2-ethylhexanoate); dibutyltin diacetate; dibutyltin oxide, trioctyltin oxide; butyltin trichloride; butyltin trimethylate; dibutyltin dichloride; diphenyltin dichloride; tributyltin chloride or stannous bis(2-ethylhexanoate).

15. A process according to claim 14 wherein the tin catalyst is butyltin tris-(2-ethylhexanoate), dibutyltin diacetate, butyltin trichloride, butyltin trimethylate or dibutyltin oxide.

16. A process according to claim 1 wherein the temperature is 150°–190° C.

17. A process according to claim 16 wherein the temperature is 160°–190° C.

18. A process according to claim 1 wherein said process is run at a pressure of between 250 and 1 mbar.

19. A process according to claim 18 wherein the process is run at a pressure of between 50 and 3 mbar.

20. A process according to claim 1 wherein the tin catalyst is not removed from the final product after the transesterification reaction is complete.

* * * * *